US009164168B2

(12) United States Patent
Petkie

(10) Patent No.: US 9,164,168 B2
(45) Date of Patent: Oct. 20, 2015

(54) SYSTEMS FOR DETECTING MOVEMENT OF A TARGET

(75) Inventor: Douglas T. Petkie, Dayton, OH (US)

(73) Assignee: Wright State University, Dayton, OH (US)

(*) Notice: Subject to any disclaimer, the term of this patent is extended or adjusted under 35 U.S.C. 154(b) by 1195 days.

(21) Appl. No.: 12/727,872

(22) Filed: Mar. 19, 2010

(65) Prior Publication Data
US 2010/0241009 A1 Sep. 23, 2010

Related U.S. Application Data

(60) Provisional application No. 61/161,784, filed on Mar. 20, 2009.

(51) Int. Cl.
G01S 13/00 (2006.01)
A61B 5/08 (2006.01)
G01S 13/58 (2006.01)
A61B 5/024 (2006.01)
A61B 5/055 (2006.01)
A61B 5/113 (2006.01)
G01S 7/35 (2006.01)
G01S 13/50 (2006.01)

(52) U.S. Cl.
CPC .............. G01S 13/583 (2013.01); A61B 5/024 (2013.01); A61B 5/055 (2013.01); A61B 5/113 (2013.01); G01S 7/35 (2013.01); G01S 13/50 (2013.01)

(58) Field of Classification Search
USPC ........................................................ 600/484
See application file for complete search history.

(56) References Cited

U.S. PATENT DOCUMENTS

| 4,926,868 A | * | 5/1990 | Larsen ........................ 600/407 |
| 4,958,638 A | * | 9/1990 | Sharpe et al. ................ 600/407 |
| 2004/0123667 A1 | * | 7/2004 | McGrath ........................ 73/704 |
| 2005/0143667 A1 | * | 6/2005 | Park et al. .................... 600/509 |
| 2010/0130873 A1 | * | 5/2010 | Yuen et al. .................... 600/484 |
| 2010/0241010 A1 | * | 9/2010 | Lin et al. ...................... 600/484 |

OTHER PUBLICATIONS

Petkie et al., Remote respiration and heart rate monitoring with millimeter-wave/terahertz radars, 2008, SPIE, vol. 7117, p. 1-5.*
Phase Locked Sources, May 2004, Herley-CTI, Inc.*
(Continued)

Primary Examiner — Etsub Berhanu
Assistant Examiner — Michael R Bloch
(74) Attorney, Agent, or Firm — Dinsmore & Shohl LLP

(57) ABSTRACT

A system is disclosed for wirelessly detecting movement of a target. The system comprises a reference oscillator, a transmitter, a receiver, a demodulator, and a processor, wherein: the reference oscillator generates references frequencies for the transmitter, the receiver, and the demodulator; the transmitter generates a continuous-wave signal at a frequency based on the transmitter reference frequency and wirelessly transmits it to the target; the receiver wirelessly receives a reflected signal from the target having a phase angle corresponding to movement of the target and converts the reflected signal into an intermediate frequency signal based on the receiver reference frequency; the demodulator demodulates the intermediate frequency signal into an in-phase component and a quadrature component; and the processor converts the in-phase component and the quadrature component into a movement signal corresponding to movement of the target.

11 Claims, 5 Drawing Sheets

(56) References Cited

OTHER PUBLICATIONS

Greneker, Eugene and Geisheimer, J.L., "The Radar Flashlight Three Years Later: An Update on Developmental Progress," 34th Annual 2000 International Carnahan Conference on Security Technology: 34rd Annual IEEE Conference, pp. 257-259.

Eugene F. Greneker, et al., The Radar Flashlight Three Years Later: An Update on Development Progress, IEEE 2000, pp. 257-259.

Yanming Xiao, et al., Frequency-Tuning Technique for Remote Detection of Heartbeat and Respiration Using Low-Power Double-Sideband Transmission in the Ka-Band, IEE Transactions of Microwave Theory and Techniques, vol. 54, No. 5, May 2006, pp. 2023-2032.

Remote Cardiovascular Sensing, QinetiQ, QinetiQ Ltd. 2002, QinetiQ/S&E/SPS/PUB021592, pp. 1-2, United Kingdom.

\* cited by examiner

SYSTEMS FOR DETECTING MOVEMENT OF A TARGET

CROSS REFERENCE TO RELATED APPLICATIONS

This patent application claims the benefit of U.S. Provisional Application 61/161,784, filed on Mar. 20, 2009.

STATEMENT REGARDING FEDERALLY-SPONSORED RESEARCH OR DEVELOPMENT

This invention was made with government support under Contract No. DAAB07-01-D-G601 awarded by the Office of Naval Research (via EOIR Technologies). The Government has certain rights in this invention.

TECHNICAL FIELD

The present disclosure generally relates to systems and methods for detecting movement of a target and, in particular, to a millimeter-wave/Terahertz radar system that can remotely monitor vital signs of an individual at distances up to 100 meters or more. The systems and methods may be used for both surveillance and medical applications.

BACKGROUND

As background, radar systems may be used to wirelessly detect movement of a target. The radar system may transmit a signal to the target and receive the corresponding reflected signal from the target. The phase angle and/or frequency of the reflected signal from the target may correspond to movement of the target. Thus, the radar system may detect movement of the target based on the phase angle and/or frequency of the reflected signal.

The target may include a human, an animal, or an inanimate object such as an airplane. If the target is a human, the radar system may be capable of determining vital signs of the human such as the respiratory rate or the heart rate of the human. If the target is an inanimate object, the radar system may be capable of determining vibration characteristics of the inanimate object.

Operating the radar system at a relatively high frequency such as, for example, at millimeter-wave/Terahertz (MMW) frequencies may allow the radar system to operate at longer distances, penetrate objects that may interfere, and offer higher resolution. Accordingly, a radar system is needed which can operate at MMW frequencies.

SUMMARY

In one embodiment, a system for wirelessly detecting movement of a target comprises a reference oscillator, a transmitter, a receiver, a demodulator, and a processor, wherein: the reference oscillator is electrically coupled to the transmitter, the receiver, and the demodulator and generates a transmitter reference frequency, a receiver reference frequency, and a demodulator reference frequency; the transmitter generates a continuous-wave signal at a frequency based on the transmitter reference frequency and wirelessly transmits the continuous-wave signal to the target; the receiver wirelessly receives a reflected signal from the target, wherein the reflected signal comprises the continuous-wave signal reflected by the target, and wherein a phase angle of the reflected signal corresponds to movement of the target; the receiver converts the reflected signal into an intermediate frequency signal based on the receiver reference frequency; the demodulator is electrically coupled to the receiver and demodulates the intermediate frequency signal into an in-phase component and a quadrature component based on the phase angle of the reflected signal, wherein the demodulator uses the demodulator reference frequency to demodulate the intermediate frequency signal; and the processor is electrically coupled to the demodulator and converts the in-phase component and the quadrature component into a movement signal corresponding to movement of the target.

In another embodiment, a system for wirelessly detecting movement of a target comprises a transmitter, a frequency modulator, a beam splitter, a reflector, an interferometer, and a processor, wherein: the transmitter generates a continuous-wave signal and wirelessly transmits the continuous-wave signal to the beam splitter; the frequency modulator is electrically coupled to the transmitter and modulates the continuous-wave signal between a first frequency and a second frequency; the beam splitter divides the continuous-wave signal into a first signal and a second signal, wherein the first signal is wirelessly directed toward the target and the second signal is wirelessly directed toward the reflector; the interferometer wirelessly receives the first signal reflected from the target and wirelessly receives the second signal reflected from the reflector, wherein a phase angle of the first signal reflected from the target corresponds to movement of the target; the interferometer combines the first signal reflected from the target and the second signal reflected from the reflector and produces an electrical signal corresponding to a magnitude of the phase angle between the first signal reflected from the target and the second signal reflected from the reflector; and the processor is electrically coupled to the frequency modulator and the electrical signal such that the processor determines movement of the target based on the electrical signal when the continuous-wave signal is transmitted at the first frequency and when the continuous-wave signal is transmitted at the second frequency.

In yet another embodiment, a method for wirelessly detecting movement of a target comprises: generating a reference oscillator having a reference frequency; generating a continuous-wave signal based on the reference frequency; wirelessly transmitting the continuous-wave signal to the target; wirelessly receiving a reflected signal from the target, wherein the reflected signal comprises the continuous-wave signal reflected by the target, and wherein a phase angle of the reflected signal corresponds to movement of the target; converting the reflected signal into an intermediate frequency signal, wherein converting the reflected signal is based on the reference frequency; demodulating the intermediate frequency signal into an in-phase component and a quadrature component based on the phase angle of the reflected signal, wherein demodulating the intermediate frequency signal is based on the reference frequency; and generating a movement signal corresponding to movement of the target, wherein the signal is based on the in-phase component and the quadrature component.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference designators (numeric, alphabetic, and alphanumeric) and in which:

DETAILED DESCRIPTION

Figure 1:
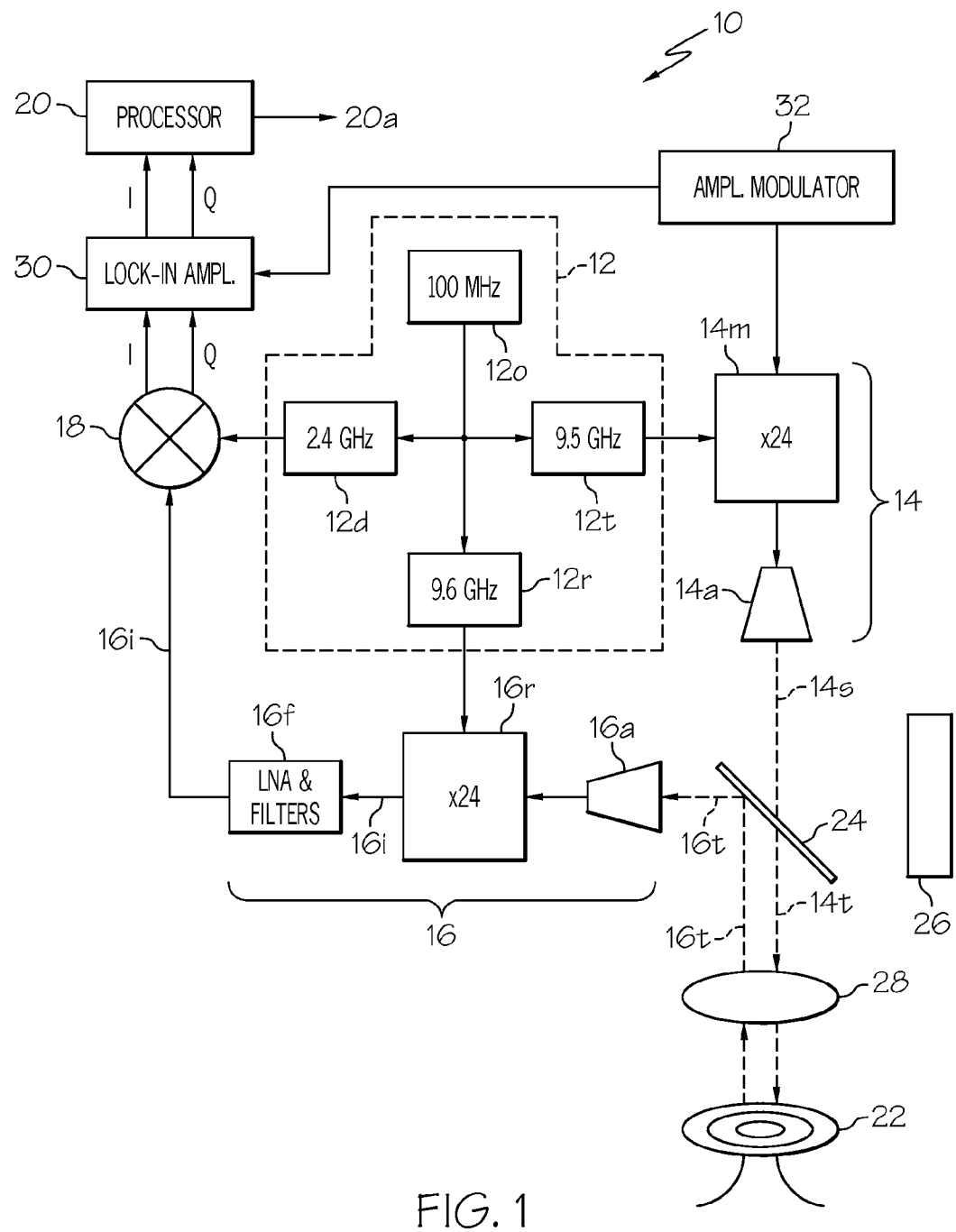
FIG. 1 depicts a radar system according to one or more embodiments shown and described herein.

According to the present disclosure, a continuous-wave MMW radar system may be used to wirelessly detect movement of a target. Such a radar system may be able to detect movement in humans, animals, and inanimate objects. For humans, the radar system may permit remote sensing of physiological characteristics of an individual such as, for example, respiratory and heart rates. The characteristics of these MMW radar systems may permit transmission of the radar signal through the atmosphere and clothing. These radar systems may also allow well-collimated (e.g., narrow diameter) beams which may improve the sensitivity of the system to small displacements. For example, the Doppler effect introduced into the reflected signal by movement of the target may be used to measure movement of an individual's chest wall due to respiration and the more subtle motion of the body due to the cardiopulmonary system (e.g., heartbeat). In accordance with one embodiment, the continuous-wave MMW radar systems may be used for remote detection of vital signs for triage, particularly in disaster scenarios where individuals may not be easily accessible such as, for example, during a flood or when disposed on a battlefield. In accordance with another embodiment, the continuous-wave MMW radar systems may be used for remote detection of vital signs to help determine intent or identify suspicious individuals near checkpoints of secured facilities. In accordance with yet another embodiment, the continuous-wave MMW radar systems may be used for remote, non-destructive evaluation and diagnostics of equipment using vibration signatures, such as, for example, engines and aircraft structures which may exhibit different vibration amplitudes and signatures based on the structural health of the equipment.

Accordingly, embodiments of the present disclosure may include continuous-wave MMW radar systems that collimate or focus the continuous-wave signal which may allow operation to distances of 100 meters or more, allow an individual to be monitored, have shorter operating wavelength (i.e., a higher operating frequency) which be more sensitive to small displacements, have good transmission through objects such as, for example, smoke and fog, have real time monitoring capabilities, and penetrate through materials such as clothing and dielectric barriers such as, for example, paint. Other features of the embodiments of the present disclosure will be apparent in light of the description of the disclosure embodied herein.

With the increased advancement in high-frequency electronics and the unique attributes of the MMW region (e.g., 30 GHz to 300 GHz), there has been an increasing effort to develop MMW radar systems for both security and medical applications. Active MMW radar systems for applications such as concealed weapon detection may also be used to simultaneously monitor subtle motion of the individual that relates to cardiopulmonary activity. In conjunction with other methods, these radar systems may improve security protection and provide the ability to assist in the detection of any suspicious individuals approaching a checkpoint or a secured facility.

Radar systems for security and health monitoring applications have been developed in the microwave and MMW region over the past several decades. Most of these systems operate from about 1 GHz to about 35 GHz using a variety of techniques and have demonstrated the detection and measurement of respiration and heart rates at a distance typically on the order of 1-2 meters and, in some instances, up to tens of meters. There may be several advantages in designing a radar system at higher frequencies. The shorter operating wavelengths may allow the system to be more sensitive to small displacements (e.g., movement) and may provide a larger Doppler shift in the reflected signal. Furthermore, the higher frequency may allow transmission through clothing which provides the ability to monitor the motion of the thorax and other locations on the body that can provide physiological signals. Also, at frequencies above 100 GHz, radiation may not be able to penetrate very far into the body due to strong attenuation from liquid water (e.g., in the skin), so reflections off the body can be more easily detected. In addition, several atmospheric windows between water lines can have significant propagation distances so the MMW radar system may be able to detect movement of targets (e.g., individuals) at distances of 100 meters or more. Lastly, the shorter wavelength may permit a more compact optical system to be designed while providing the ability to illuminate an individual in urban environments, which may greatly reduce radar clutter.

A radar system according to one embodiment may be capable of transmitting a continuous-wave signal having frequency f to the target in order to determine movement of the target. The target may reflect at least a portion of the transmitted signal, wherein the frequency and/or phase angle of the reflected signal may depend on the position and/or movement of the target. The reflected signal may be represented by the following equation:

$$R(t)=R_0 \sin(\omega_c t+\phi(t))\approx [R_0 \sin(\omega_c t)] \cos(\phi(t)), \quad \text{(Eq. 1)}$$

where $R_0$ is the amplitude of the reflected signal, $\omega_c$ is the frequency of the reflected signal, and $\phi(t)$ is the phase angle of the reflected signal which is based on movement of the target. The phase angle may be related to movement of the target by the following equation:

$$\phi(t) = \frac{4\pi}{\lambda} \times (t), \quad \text{(Eq. 2)}$$

where x(t) represents position of the target and $\lambda$ is the wavelength of the reflected signal. Changes in the position of the target, x(t), may represent movement in an axis substantially parallel to the continuous-wave signal. In this fashion, the phase angle of the reflected signal may correspond to movement of the target.

The reflected signal may also be shifted in frequency from the original continuous-wave signal due to the Doppler effect. The shift in frequency may be relatively small and may be represented by the following equation:

$$f_r(t) \approx \left(1 - \frac{v(t)}{c}\right) f_c, \quad \text{(Eq. 3)}$$

where $f_r$ is the frequency of the reflected signal, $f_c$ is the frequency of the continuous-wave signal, $v(t)$ is the velocity of the target (i.e., the first derivative of the position, $x(t)$, with respect to time), and c is the speed of light. When $v(t)$ is less than 0.01 meter/second (m/s), the velocity of the target is much less than the speed of light (i.e., $c \approx 3 \times 10^8$ m/s), and the frequency of the reflected signal is very nearly equal to the frequency of the continuous-wave signal. As an example, if the continuous-wave signal is 228 GHz and the velocity of the target is 0.01 m/s, the frequency shift is approximately 7.6 Hz. For the purposes of this disclosure, references to the frequency of the reflected signal are to be considered approximately equal to the frequency of the continuous-wave signal, unless otherwise stated.

Although the Doppler effect may produce a relatively small change in the frequency of the reflected signal, it may produce a significant change in the phase angle of the reflected signal with respect to the continuous-wave signal. Movement of the target may cause changes in the phase angle of the reflected signal, as indicated in Eq. 2. The reflected signal may be demodulated in order to recover the phase angle information contained therein. For example, after demodulation, the movement signal (indicating movement of the target) may be represented by the following equation:

$$D(t) = D_0[\cos(\phi(t) + \theta) + i \cdot \sin(\phi(t) + \theta)], \quad \text{(Eq. 4)}$$

where $D_0$ is the amplitude of the demodulated reflected signal and $\phi(t)$ is the phase change related to the movement of the target. The term $\theta$ may contain additional terms that may be dependent on the physical or electrical characteristics of the MMW radar system and may be considered constant. The term $\phi(t)$ may be represented by Equation 2, in which $x(t)$ may correspond to the position of the target, and $\lambda$ may be the wavelength of the reflected signal. Thus, the phase angle of the reflected signal may correspond to the position of the target, and changes in the phase angle of the reflected signal may correspond to movement of the target. Equation 4 may be considered to comprise an in-phase component (i.e., the cosine term) and a quadrature component (i.e., the sine term).

Changes in the phase angle of the reflected signal may correspond to movement of the target. When the target is not moving (relative to the transmitter/receiver), the phase angle of the reflected signal may be relatively constant. When the target moves toward or away from the MMW radar system, the phase angle may increase or decrease. In one embodiment, the wavelength of the continuous-wave signal may be approximately 1.3 millimeters (corresponding to a frequency of 228 GHz), and movement of the target by 0.65 millimeters (one half the wavelength) may cause the phase angle to increase or decrease 360°. The fact that movement of the target by half the wavelength produces a 360° is a result of the continuous-wave signal having to make a round trip from the radar system to the target and back to the radar system again. Since the phase angle inherently repeats every 360°, the radar system may need to track the direction the phase angle is moving and determine how many times the phase angle passes a known point such as 0°. Since the phase angle of the reflected signal may correspond to the position of the target, changes in the phase angle of the reflected signal may correspond to movement of the target. In this way, the system may be able to determine movement of the target, even when the movement exceeds the wavelength of the continuous-wave signal transmitted to the target.

FIG. 1 depicts a radar system 10 which may be capable of wirelessly detecting movement of a target 22. The radar system 10 may include a reference oscillator 12, a transmitter 14, a receiver 16, a demodulator 18, and a processor 20. The reference oscillator 12 may have a reference frequency 12o of approximately 100 MHz and may generate a transmitter reference frequency 12t, a receiver reference frequency 12r, and a demodulator reference frequency 12d. The reference frequency 12o may include a standard quartz oscillator or other suitable oscillator. For example, Model XTO-05-100-G-15P from Miteq, Inc., of Hauppauge, N.Y., may be used. It is contemplated that the reference frequency 12o may include other suitable frequencies as well. The three reference frequencies 12t, 12r, 12d may each be generated by a phase locked dielectric resonant oscillator (DRO), which may consist of a "puck" of ceramic which has a relatively large dielectric constant and a low dissipation factor. The resonant frequency of each DRO may be determined by the overall physical dimension of the puck and the dielectric constant of the material. For example, the three reference frequencies 12t, 12r, 12d may be generated by a Series PDRO model manufactured by Herley-CTI, Inc., located in Whippany, N.J. These reference frequencies may be generated by other suitable means as well. In one embodiment, the transmitter reference frequency 12t may be 9.5 GHz, the receiver reference frequency 12r may be 9.6 GHz, and the demodulator reference frequency may be 2.4 GHz. Because all three reference frequencies 12t, 12r, 12d are derived from the same reference frequency 12o, their phase angles may be synchronized such that the phase angle of each reference is "locked" with respect to each other. This characteristic may be useful for the receiver 16 and demodulator 18.

The transmitter 14 may include a frequency multiplier 14m and an antenna 14a. The frequency multiplier 14m may take the transmitter reference frequency 12t and multiply it by a fixed multiplier such as, for example, 24. In this embodiment, the transmitter reference frequency 12t of 9.5 GHz may result in the transmitter 14 producing a continuous-wave signal 14s having a frequency of 228 GHz (i.e., 9.5 GHz×24). The frequency multiplier 14m may comprise, for example, one or more frequency multipliers (e.g., Models WR4.3x3 and WR12x2b) available from Virginia Diodes, Inc., of Charlottesville, Va. If the overall frequency multiplier is 24, the frequency multiplier may comprise three frequency doublers and one frequency tripler connected in series. Other types of frequency multipliers may be used as well. The output of the frequency multiplier 14m may be fed to an antenna 14a which may wirelessly transmit the continuous-wave signal 14s to the target 22. The antenna 14a may comprise a horn antenna (e.g., Model WR3 CM from Virginia Diodes, Inc.) or other suitable device in order to wirelessly transmit the continuous-wave signal 14s to the target 22.

The radar system 10 may also include a beam splitter 24, which may be capable of splitting the continuous-wave signal 14s into two components. The beam splitter 24 may comprise thin-film Mylar or other suitable material which may split continuous-wave signal 14s into two components having approximately equal power. One component of the continuous-wave signal 14t may continue toward the target 22, while the other component may not be used by the radar system 10 and may be absorbed by an absorbent material 26 which may be disposed near the beam splitter 24 in order to absorb this unused component. The absorbent material 26 may be, for example, Eccosorb® brand absorber available from Emerson & Cuming Microwave Components located in Randolph, Mass. An absorbent material 26 from other suppliers may be used as well. The beam splitter 24 may allow the transmitter antenna 14a and the receiver antenna 16a to be coupled to the same lens 28 which may facilitate the alignment of the continuous-wave signal 14t and the reflected signal 16t from the target 22.

The component of the continuous-wave signal 14t directed toward the target may pass through a lens 28 which may collimate the continuous-wave signal 14t. The lens 28 may include a plastic or Teflon lens or, alternatively, a spherical mirror. The lens 28 may be, for example, 15 cm in diameter and may have a 50 cm focal length, thus creating a 15-cm-diameter, collimated, continuous-wave signal 14t directed toward the target 22. This may permit the continuous-wave signal 14t to be focused on the target 22 and may permit the continuous-wave signal 14t to travel further distances before diverging, thus allowing it to be more accurately focused on the target 22. Collimating the continuous-wave signal 14t may also reduce spurious reflections from objects which are not the target.

The collimated beam may strike the target 22 and may, at least in part, be reflected back toward the lens 28. The phase angle of this reflected signal 16t may correspond to movement of the target 22. The reflected signal 16t may pass through the lens 28 and be reflected by the beam splitter 24 so as to be directed toward the antenna 16a of the receiver 16. As shown in FIG. 1, the beam splitter 24 may allow the antenna 14a of the transmitter 14 and the antenna 16a of the receiver 16 to be optically coupled to the same lens 28. As such, the two antennas 14a, 16a may be at right angles to each other. Likewise, the beam splitter 24 may be at a 45° angle to both antennas 14a, 16a.

Still referring to FIG. 1, the receiver 16 may include an antenna 16a, a heterodyne receiver 16r, and low-noise amplifiers and filters 16f. The antenna 16a may be optically coupled to the beam splitter 24 such that the reflected signal 16t from the target 22 is directed toward the antenna 16a. The antenna 16a may receive this reflected signal 16t and convert it into an electrical signal suitable for the heterodyne receiver 16r. The heterodyne receiver 16r may multiply the receiver reference frequency 12r by a fixed multiplier such as, for example, 24. This multiplied signal may then be combined with the reflected signal 16t (from the target) by the heterodyne receiver 16r so as to produce an intermediate frequency 16i. The heterodyne receiver 16r may produce the intermediate frequency 16i by multiplying the reflected signal 16t by the multiplied signal. For example, if the receiver reference frequency 12r is 9.6 GHz, and the fixed multiplier is 24, the multiplied signal may be 230.4 GHz. This signal may be multiplied by the reflected signal 16t (which may be, for example, 228 GHz) so as to produce an intermediate frequency 16i of 2.4 GHz (e.g., 2.4 GHz=230.4 GHz−228 GHz). The intermediate frequency 16i may be further amplified and filtered by a low-noise amplifier and filters 16f.

The intermediate frequency 16i may contain phase angle information corresponding to the phase angle of the reflected signal 16t with respect to the continuous-wave signal 14s. As discussed herein, changes of the phase angle may correspond to movement of the target 22. Accordingly, the demodulator 18 may use the intermediate frequency 16i in order to extract the phase angle information. The demodulator 18 may comprise a multiplier which multiplies the intermediate frequency 16i with the demodulator reference frequency 12d. Both of these signals may be, for example, approximately 2.4 GHz. The output of the demodulator 18 may be two signals, I and Q, wherein I represents the in-phase component of the phase angle of the reflected signal 16t and Q represents the quadrature component (e.g., the 90° component) of the phase angle of the reflected signal 16t. Thus, the combination of Q and I may represent the phase angle of the reflected signal 16t with respect to the continuous-wave signal 14s.

The I and Q signals may be analog signals and may be positive or negative, depending on the phase angle of the reflected signal 16t. In one embodiment, the I and Q signals may be passed through a lock-in amplifier 30, which may be driven by an amplitude modulator 32 electrically coupled to the transmitter 14. The combination of the lock-in amplifier 30 and the amplitude modulator 32 may help increase the sensitivity of I and Q and may also help balance them as well. The I and Q signal may also be amplified and filtered, for example, with SRS 560 preamplifiers available from National Instruments Corporation of Austin, Tex. The amplifying and filtering may help reduce mismatches in the amplitude or offset of the I component and Q component which may be inadvertently introduced by the receiver 16 and/or demodulator 18.

The I and Q signals may be used by the processor 20 in order to determine the phase angle of the reflected signal 16t, for example, by taking the inverse tangent of Q/I. The processor 20 may have to account for the situation when I approaches zero and the inverse tangent function is undefined; this may be handled by software using filters, estimators, or other suitable methods. Other ways of determining the phase angle of the reflected signal 16t may be used as well. The output of the processor 20 may be a signal 20a corresponding to the phase angle of the reflected signal 16t. The processor 20 may be, for example, a personal computer or a programmable logic controller (PLC) executing software. In one embodiment, the I and Q signals may be digitized by a DAQ (data acquisition) board from National Instruments Corporation, which may be electrically coupled to a personal computer. After being digitized, the I and Q signals may be processed by a computer program such as Labview (available from National Instruments Corporation) or Matlab (available from The MathWorks, Inc., of Natick, Mass.). The processing of the I and Q signals in order to determine the phase angle of the reflected signal 16t (and hence movement of the target 22) may be performed in real time.

As discussed herein, one embodiment of the radar system 10 may generate a continuous-wave signal 14s having a frequency of 228 GHz. This corresponds to a wavelength of approximately 1.3 mm. The overall sensitivity of the radar system 10 may permit the processor 20 to resolve movement of the target down to about 35 micrometers (μm). Thus, the radar system 10 may be able to detect movement of the target to within a resolution of about 35 μm. Radar systems having a shorter wavelength (i.e., a higher frequency) may have a higher resolution.

Figure 2:
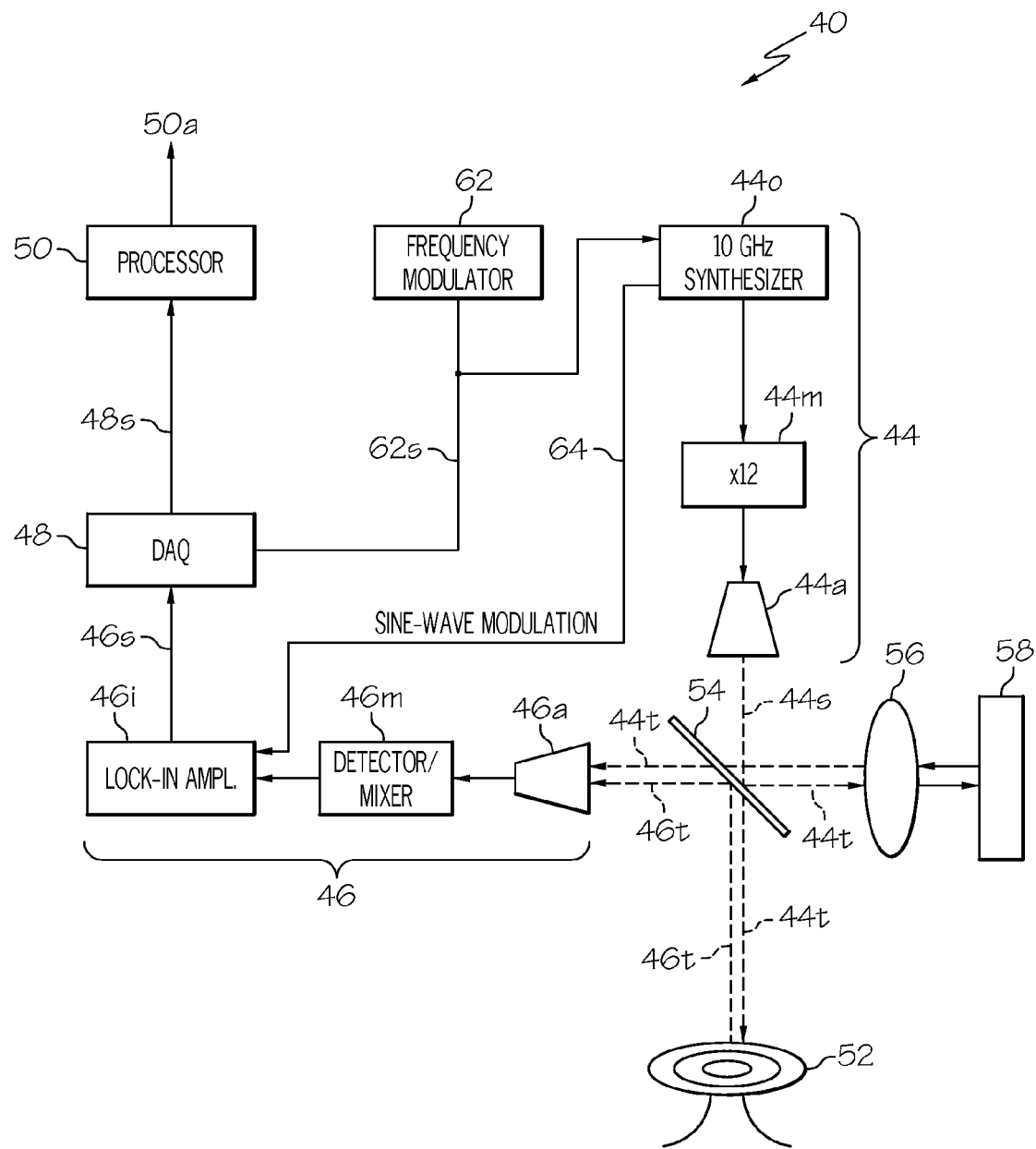
FIG. 2 depicts a radar system according to one or more embodiments shown and described herein.

FIG. 2 depicts another embodiment of a radar system 40 which may be capable of wirelessly determining movement of a target 52. The radar system 40 may include a transmitter 44, a frequency modulator 62, a beam splitter 54, a reflector 58, an interferometer 46, and a processor 50. The transmitter 44 may include a microwave synthesizer 44o, a multiplier 44m, and an antenna 44a. The microwave synthesizer 44o may be capable of dual frequency modulation (FM) at a base frequency of 10 GHz. The multiplier 44m may be an x12 multiplier chain from, for example, Virginia Diodes, Inc. (VDI), that may have both active and passive multipliers. The antenna 44a may be a horn antenna capable of wirelessly transmitting the continuous-wave signal 44s to the beam splitter 54. The transmitter output power may be approximately 1 mW at 120 GHz with an input power of about 203 mW at 10 GHz.

The continuous-wave signal 44s may wirelessly transmitted by the antenna 44a toward a Mylar beam splitter 54, where it may be split 50/50 between two paths. One path may serve as a reference signal 44t, while the other path may allow the continuous-wave signal 44t to continue to be transmitted to the target 52 being monitored. The reference signal 44t may be directed toward a lens 56 to collimate the signal followed by a reflector 58. Both the transmitter antenna 44a and the interferometer antenna 46a may be placed symmetrically with respect to the beam splitter 54 to help ensure approximately equal optical coupling. The beam splitter 54 may allow both the transmitter 44 and interferometer 46 to share the same optical path in a mono-static or co-linear optical design for the purpose of easy alignment and targeting strategies. Power may be coupled to the antennas with a 30 cm diameter spherical mirror (not shown) with focal length of 1 meter that may serve to collimate the continuous-wave signal 44s to a diameter of approximately 30 cm. The mirror position with respect to the transmitter/interferometer may be adjusted to focus the continuous-wave beam 44s to a smaller beam diameter for studying the cardiopulmonary signatures of the body, for example.

The interferometer 46 may include an antenna 46a, a detector/mixer 46m, and a lock-in amplifier 46p. A zero-biased Schottky barrier diode detector can be used as a mixer/detector 46m to demodulate the signal. The mixer/detector 46m may combine the reflected signal 46t from the target 52 and the reflected signal 44t from the reflector 58 and produce an electrical signal corresponding to the magnitude of the phase angle difference between the reflected signal 46t from the target 52 and the reflected signal 44t from the reflector 58. The lock-in amplifier 46p may be coupled to the microwave synthesizer 44o (via a sine-wave modulation signal 64) so as to improve the sensitivity of the interferometer 46. Thus, the interferometer 46 may produce an electrical signal 46s corresponding to the magnitude of the phase angle between the reflected signal 46t from the target 52 and the reflected signal 44t from the reflector 58.

A typical interferometer such as, for example, a traditional Michelson interferometer may only be able to detect the magnitude (and not the direction of) the Doppler shifted frequency and/or phase angle. While a time-frequency analysis of this signal may be used to determine movement of the target (e.g., the respiration rate), it may be more beneficial to design a system that can also be sensitive to the direction of the motion. To achieve this, the continuous-wave signal may be phase shifted, frequency shifted, or time shifted so that the phase angle of the continuous-wave signal is adjusted by 90°. This adjustment may permit the interferometer to determine the I component (when the continuous-wave signal is not adjusted) and determine the Q component (when the continuous-wave signal is adjusted by 90°). When adjusting the signal using a phase shift or time shift, the adjustment may be directly proportional to the amount of phase shift or time shift. However, when adjusting the signal based on a frequency shift, the amount of the frequency shift may depend on the distance to the target. In order to determine the distance to the target (and hence determine the correct frequency shift), one may use a FMCW-chirp (Frequency Modulated Continuous Wave) method, which may be a frequency ramp of the system over a predefined frequency range. After applying a Fourier Transform (FFT) to the time domain data of the reflected signal, the peak in the FFT may indicate the distance to the target.

In one embodiment, the radar system 40 of FIG. 2 may employ the Frequency Shift Keying (FSK) method to modulate the signal between the I and Q channels in a sequential fashion by square wave modulating the 10 GHz base frequency of the microwave synthesizer 44o. A frequency modulator 62 may be used to modulate the continuous-wave signal generated by the microwave synthesizer 44o between a first frequency and a second frequency. In the embodiment shown, the frequency may be modulated between 10.000 GHZ and 10.00375 GHz, wherein the increase of 3.75 MHz may adjust the continuous-wave signal by 90° when the target is at a distance of approximately 10 meters. Other modulation frequencies may be used as well, depending on the distance to the target. In general, the change in frequency (e.g., the second frequency minus the first frequency) in order to get a 90° phase shift may be equal to:

$$\Delta f = \frac{c}{8d}, \quad \text{(Eq. 5)}$$

where c is the speed of light and d is the distance from the radar system to the target.

For the radar system 40 of FIG. 2, Eq. 4 may be rewritten to include the phase term associated with the path difference:

$$D(t) = D_0 \cos\left(\varphi(t) + \frac{4\pi \Delta L}{\lambda} + \theta\right), \quad \text{(Eq. 6)}$$

where ΔL is the difference in the two paths of the Michelson interferometer. The term can be rewritten as 4πΔLf/c where f is the operating frequency (e.g., approximately 120 GHz), and c is the speed of light. If the frequency is square-wave modulated (or frequency shifted) such that this term shifts by λ/2, 3π/2, 5π/2, . . . , then the signal can be sequentially modulated between the I and Q channels to allow the directional Doppler signal to be calculated. For a subject at 10 meters, a frequency deviation of 3.75 MHz may be used. To increase the signal to noise ratio and mitigate the 1/f noise associated with diode detectors, a second sine-wave modulation at a rate of 50 kHz can be used with a lock-in amplifier. The frequency deviation of this modulation can be empirically set to maximize the signal to noise ratio and can also depend on the difference in path lengths. The square-wave modulation rate for the frequency modulator 62 may be 200 Hz. The electrical signal 46s may be digitized at a 10 kHz rate along with the TTL output from the frequency modulator 62 by a National Instruments DAQ board, for example. The I and Q channels can be parsed in software by using these signals, which may then be used to reconstruct movement of a target at a 100 Hz sampling rate to monitor, for example, vital signs.

Figure 3:
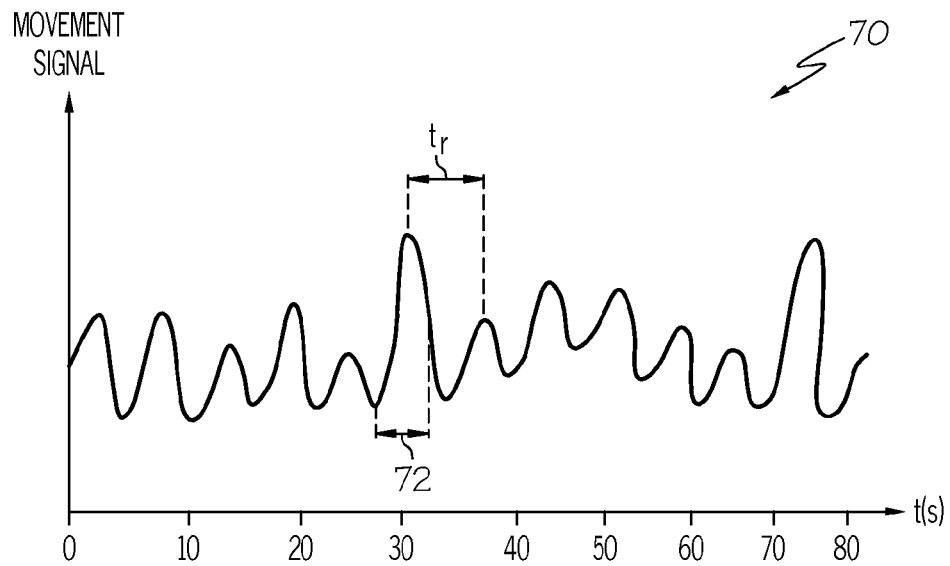
FIG. 3 depicts a graph of respiratory movement of a human according to one or more embodiments shown and described herein.
Figure 4:
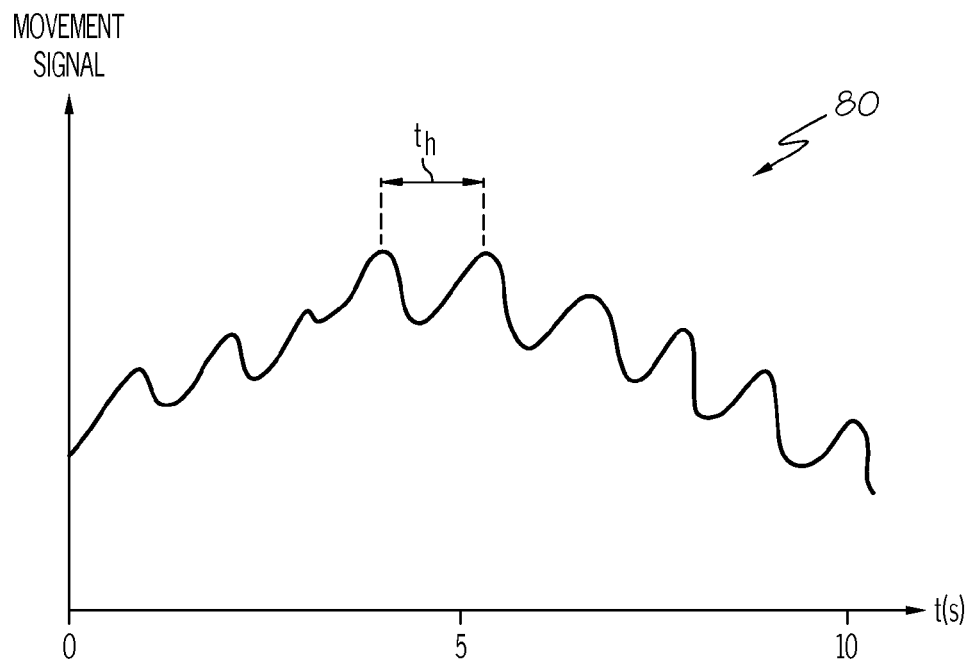
FIG. 4 depicts a graph of a heartbeat movement of a human according to one or more embodiments shown and described herein.

FIG. 3 depicts a graph 70 of respiratory movement of a human based on embodiments of a MMW radar system from FIGS. 1 and 2. The target human was approximately 8 to 10 meters from the radar system. The movement signal may have peaks and valleys which correspond to respiratory movement of the human. The x-axis of the graph 70 is time, while the y-axis is the movement signal. Based on the movement signal, it may be possible to determine the respiratory rate of the human, which may be represented by $t_r$, where $t_r$ is the time between breaths. The respiratory rate in breaths per minute may be calculated as $60/t_r$. Similarly, FIG. 4 depicts a graph 80 of heartbeat movement of a human based on one embodiment of a MMW radar system. The movement signal may have peaks and valleys which correspond to heartbeat movement of the human. The x-axis is time of the graph 80 is time, while the y-axis is the movement signal. Based on the movement signal, it may be possible to determine the heartbeat rate of the human, which may be represented by $t_h$, where $t_h$ is the time between heartbeats. The heartbeat rate in beats per minute may be calculated as $60/t_h$. Although the movement signal in FIGS. 3 and 4 may have some inconsistencies in amplitude or slope, the processor may be able to determine the respiratory rate or the heartbeat rate, respectively, of the target human based on these signals. The respiratory rate of FIG. 3 and the heartbeat rate of FIG. 4 were confirmed by using a separate monitor, the BioRadio 150 manufactured by Cleveland Medical Devices, Inc., of Cleveland, Ohio. That is, the respiratory rate and heartbeat rate as determined by the MMW radar system of FIGS. 1 and 2 were substantially the same as those determined by the BioRadio 150.

Figure 5:
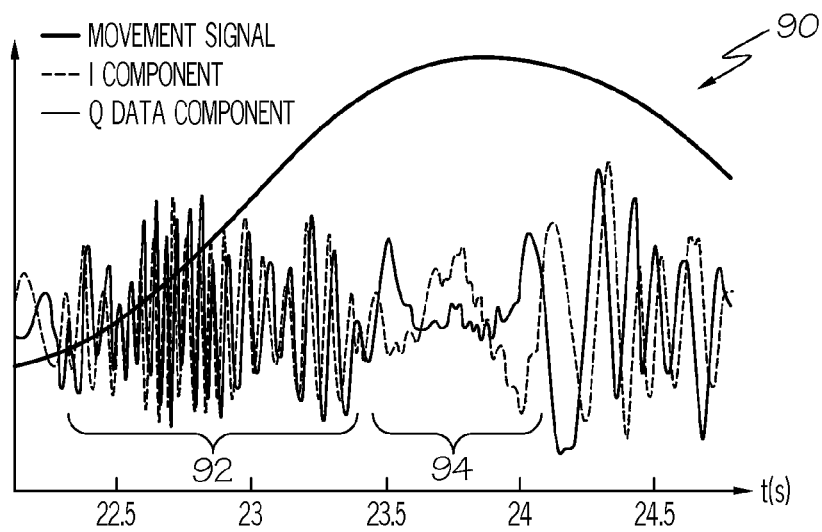
FIG. 5 depicts a graph of the relationship between the movement signal and the in-phase and quadrature components according to one or more embodiments shown and described herein.

FIG. 5 depicts a graph 90 of the relationship between the movement signal (both position and velocity) and the I and Q components. In this example, the radar system may be directed toward the thorax of a human being so that movement of the thorax may provide the respiratory rate of the individual. The I and Q components may be changing rapidly during time period 92 in which the individual is inhaling air. This rapid change in the I and Q components may indicate that the thorax is moving a distance which may be multiples of the wavelength of the continuous-wave signal generated by the radar. In one embodiment, the wavelength may be approximately 1.3 mm, such that movement of the thorax (as shown in FIG. 5) may be more than 1.3 mm such as, for example, 5 mm. During time period 94, the inhalation may have slowed (e.g., due to the lungs filling up) and the individual may be ready to exhale. As a result, the changing of the I and Q components may slow down as the movement of the thorax also slows down. As discussed herein, the direction of the movement may be determined by the sign of the I and Q components. Thus, the radar system may be capable of detecting the inhalation and exhalation of the individual and, therefore, determine the respiratory rate of the individual.

Figure 6:
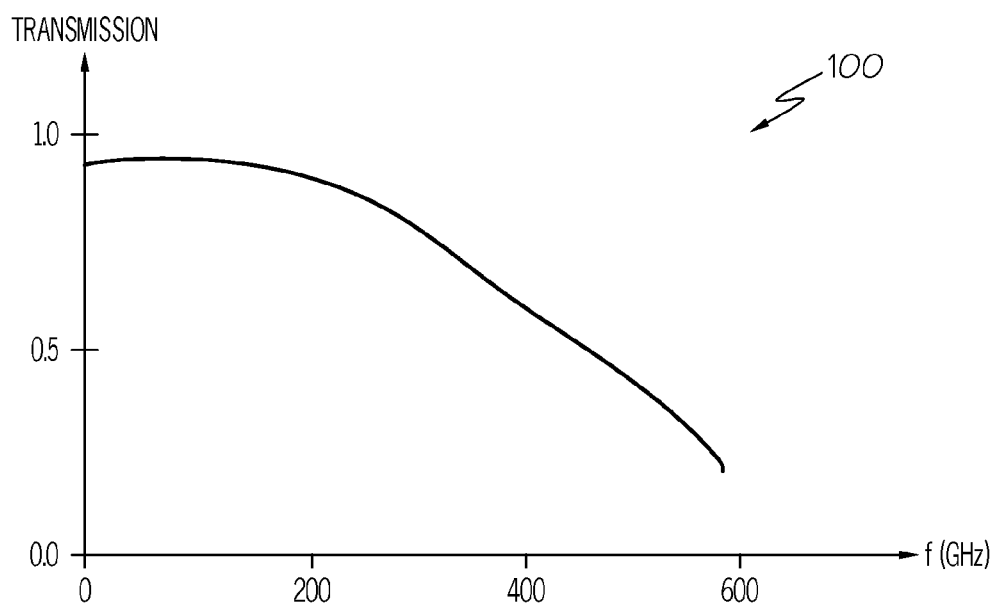
FIG. 6 depicts transmission characteristics of a MMW signal through clothes according to one or more embodiments shown and described herein.

FIG. 6 depicts a graph 100 of the transmission characteristics of a continuous-wave signal of different frequencies (and corresponding wavelengths) through clothing. Below about 300 GHz, the continuous-wave signal may transmit through clothing with very little attenuation. However, above about 300 GHz, the attenuation through closing begins to increase significantly. The graph 100 was derived empirically using different types of clothing, including scarves, pants, dresses, overcoats, etc.

Figure 7:
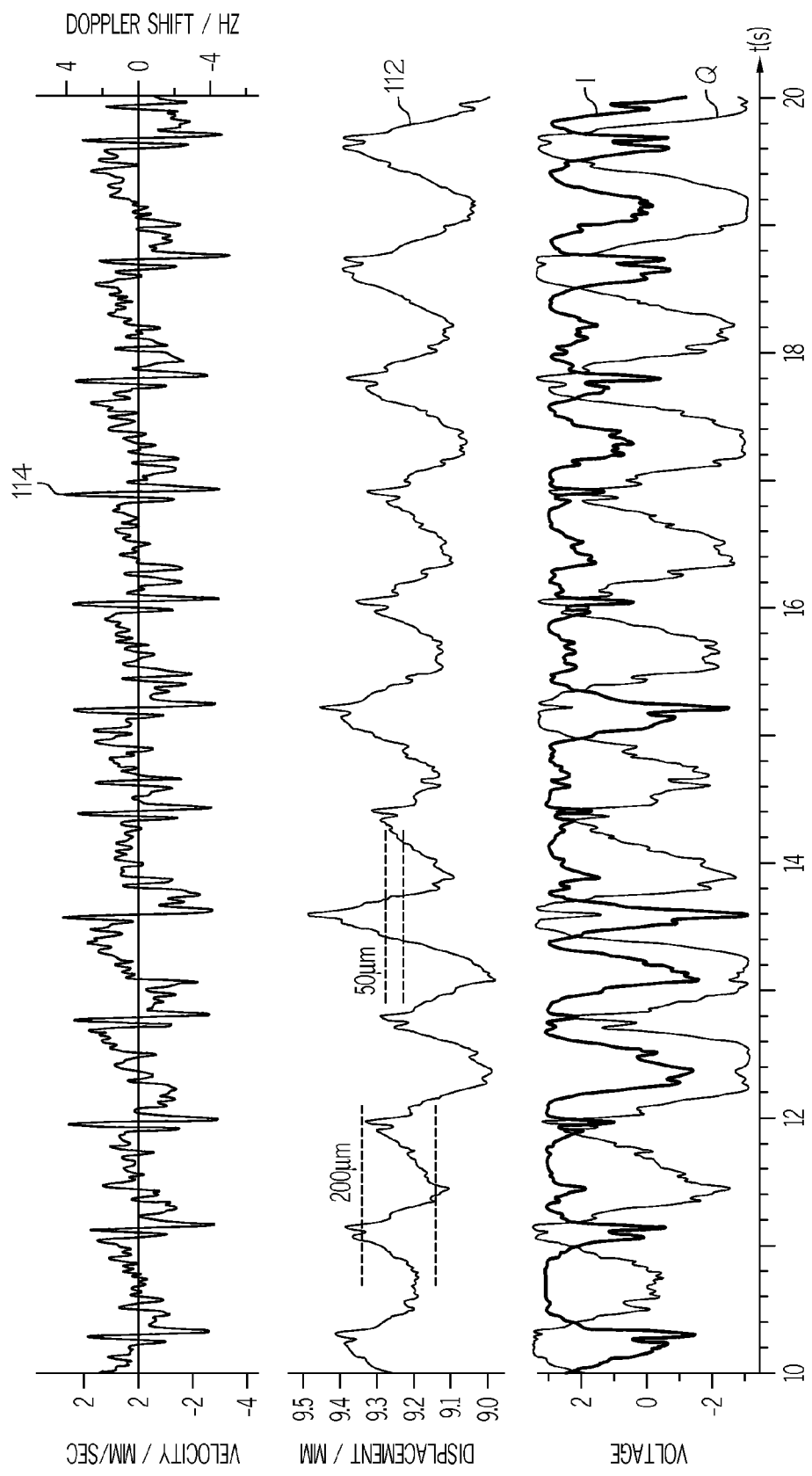
FIG. 7 depicts the relationship between the in-phase component, the quadrature component, the position of the target, and the velocity of the target according to one or more embodiments shown and described herein.

FIG. 7 depicts a graph 110 showing the relationship between the I component, the Q components, the position of the target, and the velocity of the target. Time is on the x-axis while the I component, Q component, position, and velocity are all on the y-axis. The I component and Q components are shown at the bottom of the graph 110. The position of the target 112 is shown in the middle, and the velocity of the target 114 is shown at the top. Also, the velocity of the target 114 indicates the actual velocity on the left as well as the Doppler shift in the frequency of the reflected signal on the right. This particular graph 110 shows the heartbeat rate of a human. The radar system of FIG. 1 was used to measure the target. The continuous-wave signal had a frequency of 228 GHz; thus the displacement of the target (e.g., approximately 300 μm) is less than a wavelength (approximately 1.3 mm).

It should now be understood that the systems and methods described herein may permit a MMW radar system to wirelessly determine movement of a target. The system may transmit a continuous-wave signal to the target and receive a reflected signal from the target. The system may determine changes in the phase angle of the reflected signal with respect to the continuous-wave signal in order to detect movement of the target.

It is noted that terms like "preferably," "commonly," and "typically" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A system for wirelessly detecting movement of a target, the system comprising a reference oscillator, a transmitter, a receiver, a demodulator, a beam splitter, a collimating device, and a processor, wherein:

the reference oscillator is electrically coupled to the transmitter, the receiver, and the demodulator and generates a transmitter reference frequency, a receiver reference frequency, and a demodulator reference frequency, wherein each of the transmitter reference frequency, the receiver reference frequency, and the demodulator reference frequency has a different frequency, and wherein the transmitter reference frequency, the receiver reference frequency, and the demodulator reference frequency have locked phase angles such that the phase angles are synchronized;

the transmitter generates a continuous-wave signal at a frequency based on the transmitter reference frequency and wirelessly transmits the continuous-wave signal to the beam splitter;

the beam splitter optically couples the transmitter, the collimating device, and receiver together and is configured to split the continuous-wave signal into two components wherein a first component is directed to the collimating device and a second component is not used;

the collimating device collimates and directs the first component of the continuous-wave signal to the target;

the receiver wirelessly receives a reflected signal from the target, wherein the reflected signal comprises the continuous-wave signal reflected by the target, and wherein a phase angle of the reflected signal corresponds to movement of the target;

the receiver converts the reflected signal into an intermediate frequency signal based on the receiver reference frequency;

the demodulator is electrically coupled to the receiver and demodulates the intermediate frequency signal into an in-phase component and a quadrature component based on the phase angle of the reflected signal, wherein the demodulator uses the demodulator reference frequency to demodulate the intermediate frequency signal; and the processor is electrically coupled to the demodulator and converts the in-phase component and the quadrature component into a movement signal corresponding to movement of the target.

2. The system of claim 1, wherein the reference oscillator has a frequency of approximately 100 MHz.

3. The system of claim 1, wherein the continuous-wave signal operates at approximately 228 GHz.

4. The system of claim 1, wherein the intermediate frequency signal operates at approximately 2.4 GHz.

5. The system of claim 1, wherein the target is a human, and movement of the target includes movement due to respiration and movement sue to a heartbeat.

6. The system of claim 5, wherein the processor further determines a respiration rate of the target based on the movement signal.

7. The system of claim 5, wherein the processor further determines a heartbeat rate of the target based on the movement signal.

8. The system of claim 1, wherein the receiver comprises a heterodyne receiver capable of multiplying the reflected signal with the receiver reference frequency.

9. The system of claim 1, further comprising a lock-in amplifier, wherein the lock-in amplifier is electrically coupled to the demodulator and the processor such that the lock-in amplifier increases sensitivity of the in-phase component and the quadrature component based on amplitude modulation of the continuous-wave signal.

10. The system of claim 1, wherein:
the transmitter multiplies the transmitter reference frequency by a fixed multiplier to generate the continuous-wave signal;
the receiver multiplies the receiver reference frequency by the fixed multiplier to generate a multiplied signal which is combined with the reflected signal to produce the intermediate frequency signal; and
the demodulator multiplies the intermediate frequency with the demodulator reference frequency to generate the in-phase component and the quadrature component.

11. The system of claim 10, wherein the frequency multiplier is 24 and the demodulator reference frequency is 2.4 GHz.

* * * * *